US008821788B2

(12) United States Patent  (10) Patent No.: US 8,821,788 B2
Krueger et al.  (45) Date of Patent: Sep. 2, 2014

(54) ELECTRON BEAM STERILISATION FOR CONTAINERS

(75) Inventors: Jochen Krueger, Thalmassing (DE); Heinz Humele, Thalmassing (DE)

(73) Assignee: Krones AG (DE)

( * ) Notice: Subject to any disclaimer, the term of this patent is extended or adjusted under 35 U.S.C. 154(b) by 958 days.

(21) Appl. No.: 12/546,133

(22) Filed: Aug. 24, 2009

(65) Prior Publication Data

US 2010/0054987 A1  Mar. 4, 2010

(30) Foreign Application Priority Data

Aug. 30, 2008 (DE) .......................... 10 2008 045 187

(51) Int. Cl.
 *A61L 2/24* (2006.01)
 *A61L 2/08* (2006.01)
 *B65B 55/08* (2006.01)
 *B67C 7/00* (2006.01)
 *A61L 2/10* (2006.01)

(52) U.S. Cl.
 CPC ............. *A61L 2/087* (2013.01); *A61L 2202/23* (2013.01); *A61L 2202/14* (2013.01); *A61L 2/082* (2013.01); *B65B 55/08* (2013.01); *A61L 2/24* (2013.01); *A61L 2/10* (2013.01); *B67C 7/0073* (2013.01)
 USPC .............................. 422/22; 422/186; 250/395

(58) Field of Classification Search
 USPC ................... 422/3, 22, 24, 186, 119; 250/395
 See application file for complete search history.

(56) References Cited

U.S. PATENT DOCUMENTS

| 5,378,898 | A  | * | 1/1995 | Schonberg et al. | ......... 250/492.3 |
| 6,139,796 | A  |   | 10/2000 | Kristiansson et al. | ........... 422/22 |
| 6,221,216 | B1 | * | 4/2001 | Nablo et al. | ............. 204/157.15 |
| 7,703,262 | B2 | * | 4/2010 | Till | ................................ 53/426 |
| 7,759,661 | B2 | * | 7/2010 | Avnery | ...................... 250/493.1 |
| 2005/0173020 | A1 |   | 8/2005 | Py | ................................. 141/329 |
| 2006/0192140 | A1 |   | 8/2006 | Nablo et al. | ................ 250/492.1 |
| 2007/0283667 | A1 |   | 12/2007 | Kristiansson et al. | ........... 53/426 |
| 2008/0131312 | A1 |   | 6/2008 | Kang et al. | ...................... 422/22 |
| 2008/0175752 | A1 |   | 7/2008 | Perot | .............................. 422/22 |

FOREIGN PATENT DOCUMENTS

| DE | 2 346 460 | 4/1974 | ................ A61L 1/00 |
| DE | 198 82 252 | 3/1998 | ................ A61L 2/14 |
| DE | 10 2005 043 278 | 3/2007 | ................ H05H 1/18 |
| DE | 603 08 341 | 5/2007 | ................ H05H 1/24 |

(Continued)

OTHER PUBLICATIONS

English language abstract for JP 08110310 A; published: Apr. 1996.*

(Continued)

*Primary Examiner* — Sean E Conley
(74) *Attorney, Agent, or Firm* — Hayes Soloway P.C.

(57) ABSTRACT

The method for sterilizing containers, wherein a treatment head is guided into the interior of a container to be sterilized and the treatment head emits radiation in the interior of the container at least intermittently over a predefined time period (dT), wherein the container is moved relative to the treatment head in a longitudinal direction (L) of the container at least intermittently at a relative movement speed (v) over the predefined time period (dT). The relative movement speed (v) of the treatment head located in the interior of the container varies over the predefined time period and is controlled as a function of an internal profile of the container.

32 Claims, 3 Drawing Sheets

(56) References Cited

FOREIGN PATENT DOCUMENTS

| DE | 10 2006 025 736 | 12/2007 | ................ A61L 2/14 |
| DE | 10 2007 000 305 | 1/2008 | ................ A61L 2/08 |
| EP | 1 120 121 | 8/2001 | ................ A61L 2/10 |
| EP | 1 982 920 | 4/2007 | ................ B65B 55/08 |
| EP | 1 944 044 | 7/2008 | ................ A61L 2/08 |
| JP | 08110310 A * | 4/1996 | |
| WO | WO 97/07024 | 2/1997 | ................ B65B 55/04 |
| WO | WO 99/39751 | 8/1999 | ................ A61L 2/00 |
| WO | WO 2004/013889 | 2/2004 | .............. H01J 37/04 |
| WO | WO 2007/028813 | 3/2007 | ............... H05H 1/24 |
| WO | WO 2007/137556 | 12/2007 | ................ A61L 2/14 |
| WO | WO 2008125216 | * 10/2008 | |

OTHER PUBLICATIONS

Machine translation of WO 2008125216, published Oct. 2008.*
Official Action received in corresponding German Appln. U.S. Appl. No. 10 2008 045 187.8.
EP Search Report dated Dec. 15, 2009, (5 pgs).

* cited by examiner

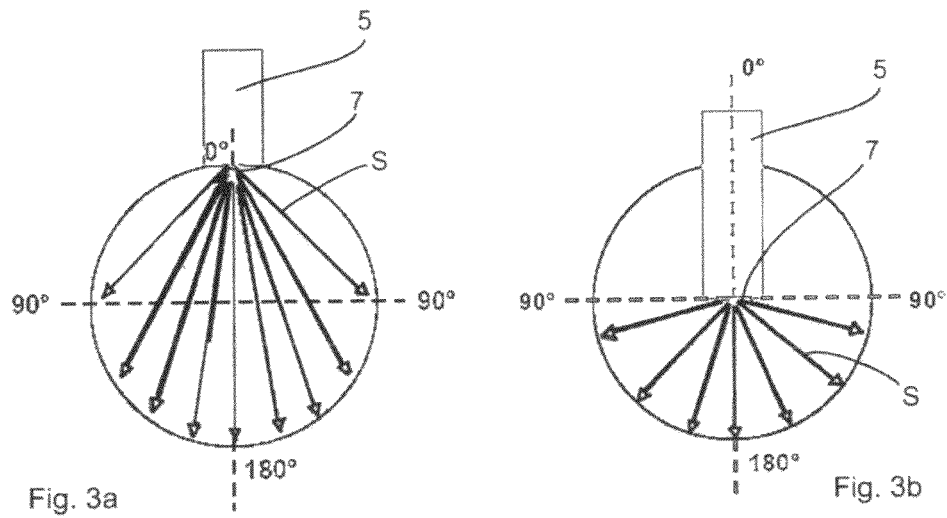
Fig. 3a    Fig. 3b
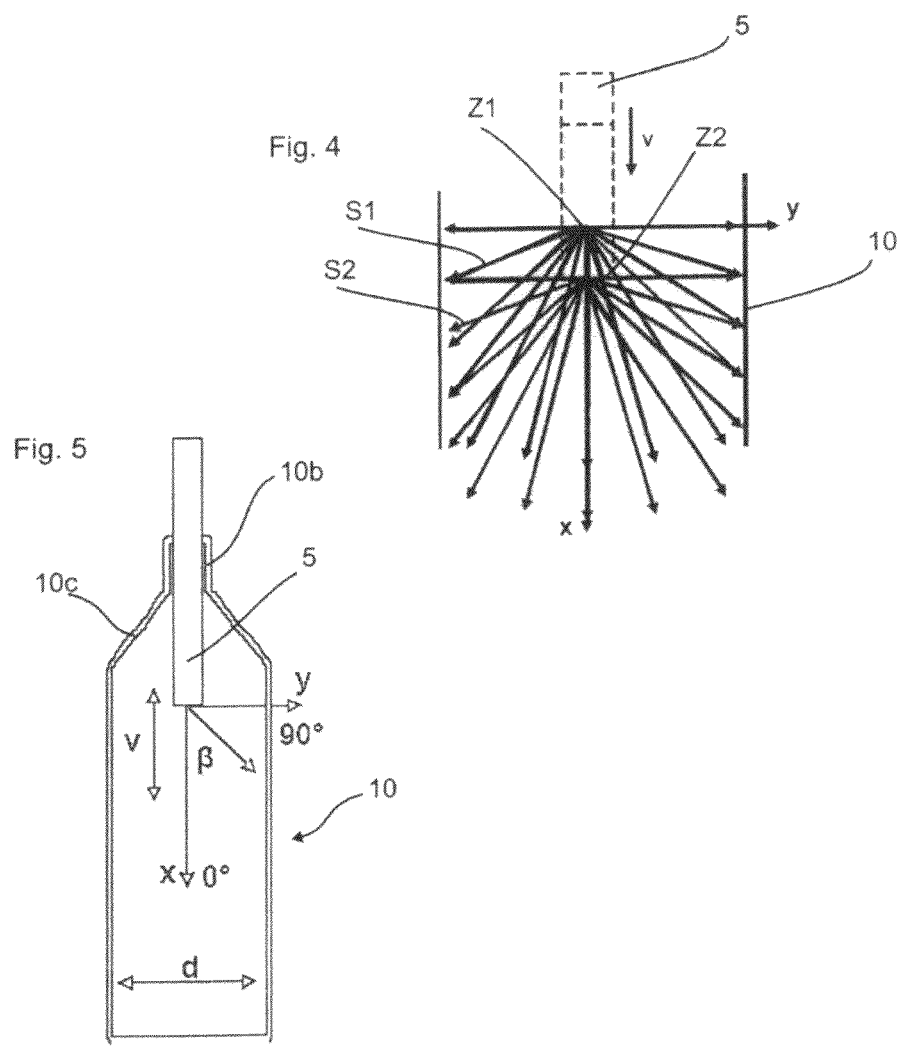
Fig. 4
Fig. 5

ELECTRON BEAM STERILISATION FOR CONTAINERS

BACKGROUND OF THE INVENTION

The present invention relates to an apparatus and a method for sterilising containers, and in particular to a method and an apparatus for sterilising containers by means of electron beams.

In the beverage-producing industry, it is known firstly to form plastic containers and then to fill said containers with a beverage. It is sometimes necessary for these containers to be sterilised, particularly on the inner sides thereof, prior to being filled. One method widely used in the prior art is sterilisation by means of sterilising gases and in particular by means of hydrogen peroxide. More recently, however, efforts are being made to reduce the use of chemicals when sterilising containers. Recently, therefore, apparatuses and methods have also become known which sterilise the containers by other measures, such as by means of ultraviolet radiation or electron beams for example.

In the as yet unpublished European patent application no. 07 007 977.7 by the Applicant, a method and an apparatus have been described in which emitting fingers, which emit the electron beams, are introduced into a container and the container is displaced relative to this emitting finger in the longitudinal direction of the container for the purposes of sterilisation. With this procedure, an efficient sterilisation of the interior of plastic containers is possible. However, it must nevertheless be noted that the containers cannot be acted upon by radiation in any random manner for the purposes of sterilisation, but rather this radiation must be subject to both maximum and minimum limit values with regard to its intensity. The minimum values are determined by the dose necessary to achieve efficient sterilisation of the containers, which in turn depends on many factors, for example on the germs to be killed. The maximum dose is limited by the fact that no damage should occur on the container to be sterilised.

The object of the present invention is therefore to provide a method and an apparatus which allows a more accurate dosing of the radiation intensities applied to containers. The sterilisation of containers by means of radiation is also intended to be improved.

SUMMARY OF THE INVENTION

In a method according to the invention for sterilising containers, a treatment head is guided into the interior of the container to be sterilised and the treatment head emits radiation in the interior of the container over a predefined time period, wherein the container is moved relative to the treatment head in a longitudinal direction of the container at least intermittently at a relative movement speed over the predefined time period. According to the invention, the relative movement speed of the treatment head located in the interior of the container varies over the predefined time period and is controlled as a function of an internal profile of the container.

It is therefore proposed according to the invention to control the movement speed of the treatment head relative to the container, and thus also the movement speed of the location at which said radiation emerges, as a function of a profile of the container. A variation of the movement speed is understood here to mean a variation of the movement speed in a certain movement direction and in particular not a change of sign of the movement speed.

It is possible both that the treatment head is stationary and the container moves relative thereto in its longitudinal direction. It would also be possible that the treatment head moves in a longitudinal direction of the container or that both the container and the treatment head move.

Preferably, the emission of radiation and the movement in the longitudinal direction take place simultaneously at least at times and preferably completely. However, it would also be possible that the movement takes place bit by bit and radiation is in each case emitted in the rest breaks.

By changing the movement speed, an adaptation to different profiles of the bottle can be achieved. For example, it is possible that the treatment head is moved more quickly while it passes the mouth of the container, since in this case the internal wall of the container is located close to the treatment head. The internal profile of the container is understood here to mean in particular the internal wall of the container, in particular with respect to the treatment head.

In general, at least one parameter which is characteristic of a radiation intensity relative to the internal surface is controlled during the movement. It would thus also be possible to control, instead of the movement speed, the intensity emitted by the treatment head, for example via a change in the acceleration voltage in the case of electron emitters. In addition, a counter-voltage could also be used.

Furthermore it would also be possible, depending on the internal profile of the container, to achieve a greater or lower absorption of the radiation before the latter reaches the container. This would be possible for example in that a cooling of the treatment head is carried out deliberately at certain times and the cooling medium attenuates the emitted radiation or the radiation striking the internal wall of the container. Absorption elements could also be provided, which absorb the radiation in a predefined and variable manner.

In one preferred method, the treatment head emits charge carriers. In this case, the treatment head or even a different element may comprise an electron emission source and also an acceleration device which accelerates these electrons towards an exit window. The sterilisation of the internal walls of the container is brought about by means of these exiting electrons.

In a further preferred method, the movement is controlled by a control device on the basis of data stored in a memory device, wherein these data are characteristic of cross-sections of the container in the longitudinal direction of the container. For example, the movement speed of the treatment head relative to the container can be reduced in those portions of the container in which the latter has a larger cross-section, and the movement speed of the treatment head relative to the container can be increased in those portions in which the cross-section is reduced.

It is thus possible that this relative movement between the treatment head and the container is programmed via predefined travel profiles. In this case it is possible to create an overall travel profile for the entire irradiation process and preferably to break said profile down into individual curve segments. Different stroke speeds and optionally also accelerations can in this case be assigned to the individual stroke movements of the container. This division is advantageous in order to obtain a better adaptation to the geometry of the container.

It is possible in this case to specify for such a curve segment the start and end point, i.e. the stroke distance, and also the necessary travelling speed, i.e. the stroke speed. These individual curve segments can then be combined to form an overall curve which corresponds to the travel profile. The stroke distances and travel durations of the individual curve segments can in this case be summed, so that they result overall in the total stroke and the total process duration of the travel profile. It is possible in this case for kinks to occur between the individual segments, at which different speeds of the travel profile merge into one another. However, it would also be possible to avoid such kinks via a further control and to achieve a smooth (i.e. mathematically differentiable) speed profile through appropriate accelerations and slowing.

In a further preferred method, the movement of the treatment head is controlled as a function of a diameter of the container. It must be noted here that electrons exiting in particular from the treatment head have a certain range and lose a certain proportion of their energy over the path length traveled. Particularly in large-diameter regions of the container, therefore, it is necessary for the time of action to be accordingly longer so as to compensate for the correspondingly lower energy of the electrons.

In a further preferred method, the movement of the treatment head is also controlled as a function of an angle at which the internal wall of the container extends relative to the longitudinal direction of the container. For example, a container portion which widens from the top downwards is often provided in the mouth region of a container, which portion of the container can be reached only with difficulty by the exiting electron radiation. Also in these regions, therefore, the movement speed should be reduced.

As mentioned above, the movement is particularly preferably controlled on the basis of a programmed travel profile. This travel profile can be determined on the basis of empirical data for corresponding containers, but it would also be possible to determine this travel profile on the basis of parameters of the container, such as the curvature and the cross-section for example.

Preferably, the container itself is moved in its longitudinal direction and thus with particular preference the treatment head or the emitting finger is kept at a constant height. For this purpose, a carrier device may be provided, on which there is in turn arranged a clamp which moves the container itself upwards or downwards in its longitudinal direction.

In a further preferred method, the travel profile is determined by guiding a treatment head into the interior of a container or reference container and by the treatment head emitting radiation in the interior of the container, wherein the container is moved relative to the treatment head in a longitudinal direction of the container during the emission of the radiation and a large number of characteristic data are recorded which are characteristic of radiation striking an internal wall of the container. In this method, therefore, a reference dose which the treatment head applies to the internal wall of the container is determined. It is also possible here that the emission of the electron radiation takes place at the same time as the movement, or also that the emission and the movement alternate at least partially.

In one preferred method, a material which reacts to the radiation emitted by the treatment head and which in this way allows conclusions to be drawn about the intensity of this radiation is applied to the internal wall of the container. It is thus possible for example to carry out a dose measurement by means of an irradiated measurement film, wherein this measurement film is applied to the internal wall of the container. In this way, the dose distribution in the treated containers can be determined. These measurement strips change colour as a function of the dose intensity and can be evaluated by means of a dose measuring device. In this case it is possible for the measurement film to be hidden by a corresponding plastic carrier in order in this way also to simulate the effects which occur in the interior of the container wall. In addition, a dye may be applied to the measurement film. Under the effect of the radiation, the film changes colour to certain colour shades in a manner proportional to the absorbed quantity of energy. These colour shades can then be read by means of a dose measuring device and thus indicate which dose has been applied for example in kilograys (kGy).

In a further method according to the invention, a travel profile for the internal sterilisation of containers is determined, wherein a treatment head is guided into the interior of the container and the treatment head in the interior of the container directs radiation onto an internal wall of the container, wherein the container is moved relative to the treatment head in a longitudinal direction of the container preferably during the emission of the radiation. According to the invention, a large number of data are recorded which are characteristic of radiation striking an internal wall of the container. This determination method is closely correlated with the invention described above, since in particular the abovementioned travel profile for the later operating mode can be determined using the data thus determined.

However, it is also possible to carry out this measurement method independently of the actual operating method described above. Preferably, a large number of containers are measured using the described measurement method and the data from these containers are stored in a database which can be used during the subsequent operating method. It is also possible to treat new containers, which are similar to containers already measured, by adapting the values determined for these measured containers. It would also be possible to divide the containers to be measured into portions, for example according to similar head or base portions, and in this way to allow the measured values obtained to be used for a larger number of containers, for example if a certain container is similar to a first measured container with regard to its head region and is similar to a second container with regard to its base region.

The present invention also relates to an apparatus for sterilising containers, wherein this apparatus comprises a treatment head which is configured in such a way that it can be guided into an interior of a container to be sterilised. This treatment head comprises a radiation source which emits radiation, and the apparatus comprises a movement device which moves the container relative to the treatment head in a longitudinal direction of the container at a predefined movement speed, while the treatment head emits radiation at least intermittently. According to the invention, the apparatus comprises a control device which varies this relative movement speed of the treatment head located in the interior of the container and controls said relative movement speed as a function of an internal profile of the container.

Preferably this is a treatment head which can be introduced into the container through a mouth, wherein this mouth has a smaller cross-section than a main body of the container for example. The movement device may be a drive, such as in particular but not exclusively a linear motor, which moves the container as a function of a predetermined travel profile.

Preferably, the radiation source emits charge carriers and in particular electrons. However, it would also be possible that a different type of radiation is emitted, such as for example X-ray radiation, UV radiation or the like. The basic concept of this invention can also be applied to these other types of radiation.

In a further advantageous embodiment, the apparatus comprises a memory device, in which a travel profile characteristic of the movement of the treatment head is stored. As mentioned above, this travel profile may be obtained from empirical data which were determined for a certain type of bottle. However, it would also be possible that the travel profile is obtained at least partially on the basis of theoretical considerations which take account of for example the cross-section of a container and also the angle of inclination of the container wall.

In a further advantageous embodiment, the apparatus comprises an image recording device which records an image of a container to be sterilised. In this case, the data of this image recording can be used for the speed control. For example, it would be possible that an image of a container is recorded in an operating mode and then image processing software compares this image with a plurality of images for stored containers. As soon as a corresponding container has been found, a corresponding travel profile can be loaded and the movement of the treatment head can be controlled on the basis of this travel profile during the operating mode.

However, it would also be possible that an image is recorded and the geometries of the container are determined on the basis of this image, and the travel profile for the treatment head is controlled on the basis of these geometries. It would also be possible that mixed variants of the two aforementioned methods are used, so that the travel profile is controlled both on the basis of direct geometrical considerations and on the basis of empirical data.

In a further preferred method, the apparatus comprises a plurality of treatment heads which are arranged one behind the other on a transport device. In this case it is possible that both bottle holders, such as gripping elements for example, and the treatment heads are arranged on the same transport device and thus are moved synchronously with one another. Preferably, the containers are moved during their sterilisation, for example on a transport carousel on which the corresponding treatment heads are also moved at the same time. In this way, a high throughput of containers can be sterilised one behind the other.

It is possible to sterilise internally both containers which have already been formed and preforms before they are formed.

Such an apparatus can thus be configured either as a rotary unit or as a linear unit. It is possible that the entire apparatus is accommodated in a treatment chamber which serves for both the internal and the external sterilisation of containers and in particular PET containers by means of electron radiation. The sterilisation unit itself may also be integrated in a stretch blow moulding machine or in a filling device or may also be arranged as a stand-alone unit. The latter variant offers the advantage that existing lines can optionally be retrofitted. Integration in a stretch blow moulding machine or in a filling device offers the advantage that in this way the costs of overall production can be reduced.

It is also possible that the containers are transferred via star-wheels, for example star-wheels which handle the containers by the neck, to the sterilisation unit, where they are moved over the treatment head or emitting finger by means of a linear stroke movement.

Preferably the beam generator used is a compact electron emitting unit with an emitting finger which, as mentioned above, is dimensioned in such a way that it can dip into the bottle in order to apply the electron cloud with the lowest possible energy to the internal surface of the container. In the context of a rotary machine arrangement, it would be possible that suitable transformers or mains devices for the electron beam generators run along with the latter on a carousel, thereby making it easier to supply the high voltage.

The possibility of improved surface treatment or sterilisation for in particular even complex-shaped beverage containers by electron beams can be achieved by the linking of electronic and mechanical components. In this way, despite the three-dimensional expanse of the containers, the most homogeneous possible dose distribution can be achieved on the internal surface of the containers. The substrate to be treated or the container is preferably moved relative to a stationary radiation source, with the course of the movement being adapted to the applied dose intensity as mentioned above.

BRIEF DESCRIPTION OF THE DRAWINGS

Further advantages and embodiments will emerge from the appended drawings:

In the drawings:

FIG. 3a shows an example of a radiation distribution in the interior of a hollow container;

FIG. 3b shows another example of a radiation distribution in the interior of a hollow container;

FIG. 4 shows an example of a radiation treatment in the interior of a cylindrical container;

FIG. 5 shows a schematic view to illustrate the relevant radiation parameters;

DETAILED DESCRIPTION OF THE DRAWINGS

Figure 1:
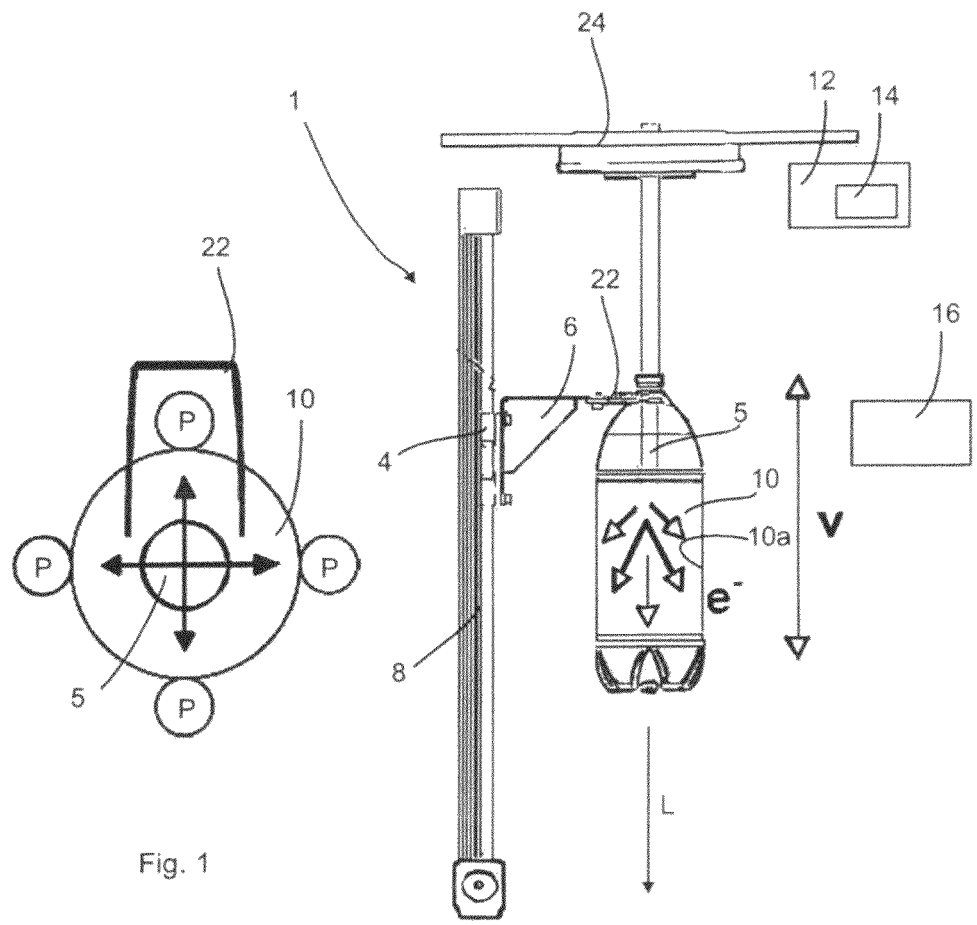
FIG. 1 shows a schematic view of a sterilisation device according to the invention.

FIG. 1 shows a schematic view of an apparatus 1 according to the invention, which may form part of an installation for treating containers. Here, reference 10 denotes a container which comprises an internal wall 10a that is to be sterilised by means of electrons denoted $e^-$. Reference 5 denotes a treatment head which can be introduced into the interior of the container 10. Here, this treatment head 5 is arranged in a stationary manner in the longitudinal direction L of the container and is arranged on a carrier 24. The electrons are accelerated under a high vacuum and are emitted through an electron exit window (not shown in detail here). The electrons are scattered at air molecules, so that an electron cloud forms which serves to sterilise the internal wall 10a of the container 10.

In a further preferred embodiment, the apparatus or the treatment head 5 comprises an inner housing, within which the acceleration device is arranged, and an outer housing surrounds this inner housing. With particular preference, a vacuum is applied in the interior of this inner housing, in which preferably the charge carrier generation source and the acceleration device are provided. Particularly preferably, a space which extends as far as the treatment head is formed between the outer housing and the inner housing, through which space a medium and in particular a gaseous or liquid medium can be guided.

This gaseous medium serves in particular for cooling the exit window, and for this purpose the gaseous or liquid medium is guided along the inner housing to the treatment head and also past the exit window. A space in the form of a channel or a plurality of channels is thus preferably formed between the outer housing and the inner housing, wherein with particular preference a lower end portion of the outer housing is configured in such a way that the gas flow is also guided past the apparatus and thus also the exit window in the radial direction for example. It is pointed out that the flow of the gaseous medium does not reach, or least does not directly reach, the internal wall of the container, but rather, as mentioned, is in particular guided past the exit window.

The container 10 is held by a gripping clamp 22 which is arranged on a carrier 6, the latter in turn being arranged on a linear drive 4. Reference 8 denotes a holder, along which the linear drive 4 can move in the longitudinal direction L. The container 10 is thus also moved in the longitudinal direction L. As mentioned above, the drive is preferably a linear motor. It would also be possible to arrange this linear motor below the container or else above the treatment head, so that no deflection or one-sided deflection of the electrons by the linear motor takes place. The clamp 22 and also the carrier 6 may be made from a plastic which does not exert any forces on electrons. Reference v denotes the speed at which the relative movement between the treatment head 5 and the treatment container 10 takes place.

A relative movement of the bottle in the electron beam thus takes place, wherein as a result an adaptation of the dose distribution is possible through a programmable travel profile. The apparatus shown in FIG. 1 can also be used to form a reference profile. For this purpose, one or more measurement strips can be applied to the internal surface of the containers 10. The measurement strip preferably points in the irradiation direction which is to be evaluated. It is possible for example to divide the internal wall of the container into four radiation positions P, which are shown in the left-hand diagram of FIG. 1.

Here, the gripping element for the container is arranged at the top position and the other positions are distributed in the clockwise direction around the internal wall of the container. As mentioned above, the purpose of this optimisation of the travel profiles is so that neither an excessively large dose nor an excessively small dose is applied in the selected bottles. Furthermore, the treatment time of the containers and the radiation intensity should be kept as small as possible.

Advantageously, the entire movement in the longitudinal direction of the container is finished within one to two seconds. The treatment time refers to the time period during which the treatment head is located in the bottle. A total cycle is thus composed of an inward travel time, a treatment time and an outward travel time. It is possible both that the radiation is emitted during the movement and that the movement is successively stopped and radiation is emitted during the rest phases.

Furthermore, a shield (not shown) which is made in particular from lead is preferably provided in order to shield any X-ray radiation. In addition, gases such as ozone and nitrogen oxides that are produced can be removed by suction.

In order to reach a starting point for the dose distribution in the container, the container is firstly moved over the treatment head at a constant speed. The container is then moved back to its basic position at the end point under the same radiation conditions, without any pause. By virtue of this procedure, a radiation profile for the container under the predefined conditions can be determined with the aid of the dose metering film. This radiation profile can then be stored and used as a basis when treating future containers. Reference 16 denotes an image recording device for recording images of the containers. On the basis of such images, the containers can be identified and the correct travel profiles can be loaded according to an identified container.

Reference 12 denotes a control device (shown only schematically) which controls the movement of the container in the longitudinal direction. A memory device 14 is also provided, in which travel profiles for controlling the movement are stored. This control device can also control the emission of electrons by the treatment head 5.

Figure 2:
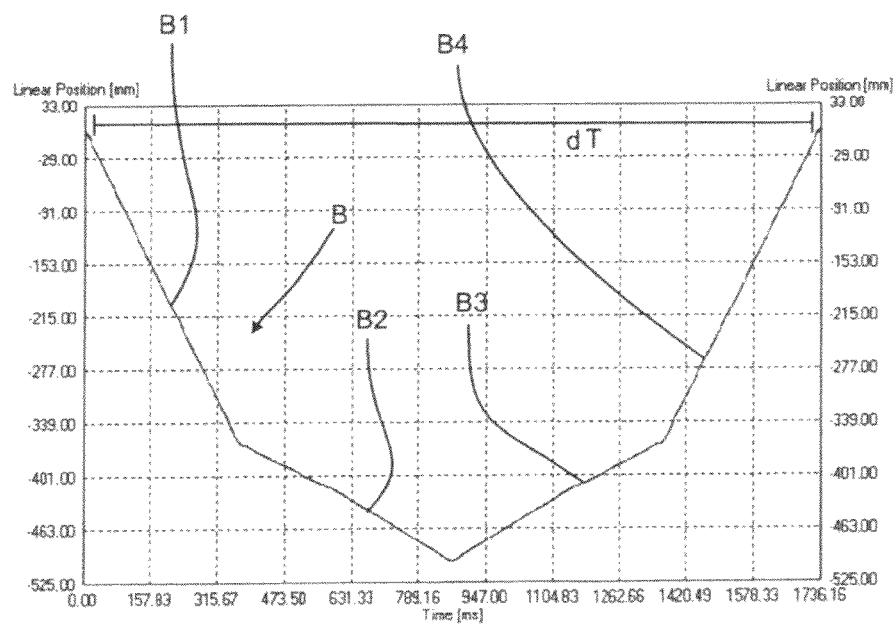
FIG. 2 shows an example of a travel profile of a treatment head.

FIG. 2 shows a movement profile for a container relative to an emitting finger. Here, a linear position in millimeters is plotted on the left coordinate and a time in milliseconds is plotted on the ordinate. In this case, the complete travel or movement profile B is composed of four segments B1-B4, wherein here a symmetrical movement profile is used. The individual segments B1-B4 merge into one another via kinks but, as mentioned above, this is not absolutely necessary.

Instead, a smooth movement can also be achieved by means of suitable speed control. In the diagram shown in FIG. 2, the movement direction reverses directly between the segments B2 and B3. However, it would also be possible that the container remains at a standstill for a brief period of time, and electron radiation is emitted during this time. Reference dT denotes the time period within which the sterilisation of the containers 10 takes place. Within this time period, therefore, both the relative movement of the treatment head 5 relative to the container 10 and also the emission of electrons take place.

It is possible that the entire travel profile B is determined on the basis of measurements which were carried out on one specific container. However, it would also be conceivable that different segments are based on measurements carried out on different containers. For example, the segments B1 and B4 describe the movement of the treatment head 5 in an upper region of the container 10 and the segments B2 and B3 describe the movement in a lower region of the container. It would be possible here that the segments B1 and B4 are based on measurements carried out on a first reference container and the segments B2 and B3 are based on measurements carried out on a second reference container.

FIGS. 3a and 3b show a measurement set-up for a container with a spherical internal cross-section. In the left-hand diagram, the treatment head 5 or the exit window 7 thereof is applied to the upper end of the container 10 and in FIG. 3b is applied in the centre of the container 10. It can be seen that different radiation distributions S are obtained also depending on the position of the treatment head 5 relative to the interior of the container. In particular, the path lengths of the radiation in the variant shown in FIG. 3b are shorter than in the position shown in FIG. 3a, and thus a more intensive irradiation of the lower hemisphere of the container 10 takes place in the case of the embodiment shown in FIG. 3b.

Once the experiments shown in FIGS. 3a and 3b have been carried out, the dose metering films applied in the interior of the containers can be removed and evaluated.

FIGS. 4 and 5 show a further experiment to determine a travel profile. It can be seen that the dose distribution depends on the process parameters stroke speed (v), bottle geometry (d, β), acceleration voltage, radiation current and treatment duration. Here, the speed v is correlated with the diameter d and the opening angle β of the container. Since, depending on the geometry of the container, a homogeneous dose distribution does not occur at a constant stroke speed, the stroke speed is varied as mentioned above.

FIG. 4 shows a treatment head 5 in two different positions, i.e. the respective centre Z1, Z2 at which the exit window is located is shown at two different positions in FIG. 4. Accordingly, different radiation distributions S1 and S2 on the internal wall of the container can also be seen. Proceeding from the start position in FIG. 4, i.e. the upper position of the treatment head, the dose is applied to the bottle wall through the scattering dome. If the emitting finger travels into the target position at a speed v, this scattering dome also moves and the newly applied dose is superposed with the dose from the start position. The dose that can be achieved on the internal wall of the bottle thus also depends on the dose applied previously by the treatment head. Reference 10b in FIG. 5 denotes a mouth of the container, and reference 10c denotes the mouth region of the container 10 which is located below said mouth 10b and within which the cross-section d of the container 10 widens.

The level of the radiation intensity, i.e. the acceleration voltage and the radiation current, depends on the bottle to be treated and the reference germ to be treated. The greater the resistance of this germ and the greater the bottle dimensions, the higher the radiation intensity must be set. For the thickness of the electron exit window 7, a titanium film having a thickness in a range from 7-13 μm proves to be particularly suitable. This thickness ensures, by means of active air cooling, a sufficient stability against the effect of heat of the electron beam.

Furthermore, as the thickness of the titanium film increases, said film has a negative effect on the sterilisation result. A thicker film absorbs more radiation energy than a thinner film and consequently in this case there is less energy available for applying the dose.

Figure 6:
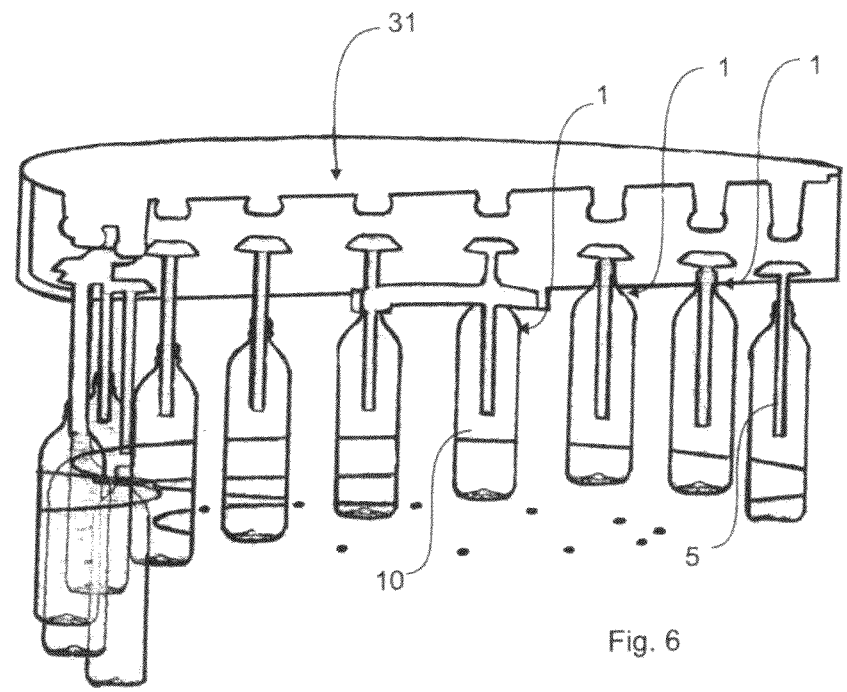
FIG. 6 shows a schematic view of a plurality of apparatuses according to the invention arranged on a transport device.

FIG. 6 shows a schematic view of the revolving wheel 31. This revolving wheel 31 comprises a plurality of apparatuses 1 according to the invention which are in each case arranged at the same height, but it can be seen that the individual containers 10 are each case lifted to a maximum position and in this way the treatment head or the emitting finger 5 is dipped into the containers 10 to varying depths depending on the rotary position. During this entire procedure, the apparatuses 1 according to the invention are activated and in this way the internal wall of the containers 10a is sterilised over the entire height of the containers 10. The length of the emitting fingers 5 is selected so that also an effective sterilisation of the bottoms of the containers 10 is possible.

Figure 7:
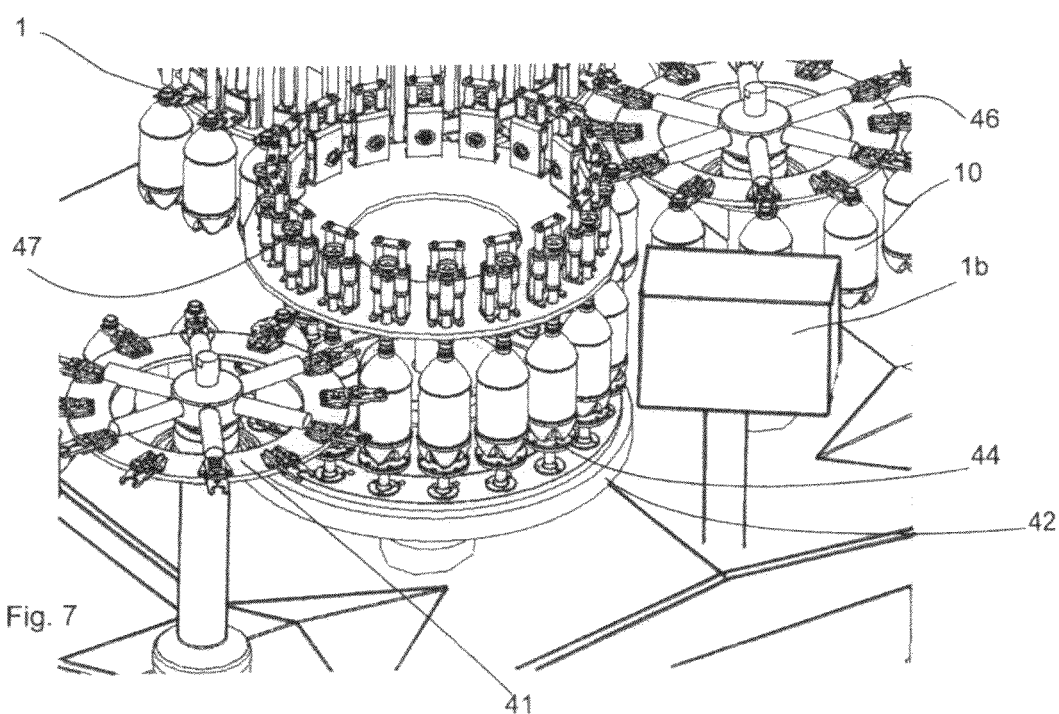
FIG. 7 shows a view of an installation comprising a plurality of apparatuses according to the invention.

FIG. 7 shows a perspective view of an arrangement according to the invention. Provided upstream of a plurality of apparatuses 1 according to the invention is a further transport carousel 42, on which the containers are transported. The containers are guided past a further sterilisation apparatus 1b for containers and are sterilised on their outer wall by this further sterilisation apparatus 1b. The interior of the containers 10 is then sterilised as described above.

Reference 44 denotes rotary devices such as rotary plates, by means of which the containers 10 are rotated about their longitudinal direction (or longitudinal axis). By virtue of this rotation, a larger area of the outer circumference of the containers 10 can be sterilised. It would also be possible to provide a plurality of sterilisation apparatuses 1b one behind the other in the transport direction of the containers 10.

The electron-emitting apparatus was described in detail in the European patent application no. 07 007 977.7 by the Applicant. The content of said patent application is hereby also incorporated in its entirety by way of reference in the disclosure of the present application.

Furthermore, it would also be possible that the container 10 is placed under a (partial) vacuum during the emission of the electron radiation. By virtue of this procedure, the range of the electrons after exiting from the exit window 7 can be increased. It is also possible that such a partial vacuum is applied already before the start of electron emission. This procedure comes into consideration both for the sterilisation of preforms and for the sterilisation of containers 10 that have already been formed.

In order to achieve such a (partial) vacuum in the interior of the containers 10, a sealing device (not shown) could be arranged for example on the outer circumference of the treatment head 5, which sealing device on the one hand is movable relative to the treatment head 5 in the longitudinal direction thereof and on the other hand seals off the space between the treatment head 5 and the mouth 10b of the container 10 when the treatment head 5 enters the container 10. An opening could in turn be arranged in this sealing device, via which opening air can be sucked out of the container 10 in order to generate a (partial) vacuum in the interior of the container 10.

The entire apparatus or even a plurality of such apparatuses could also be arranged in a chamber or a housing to which a (partial) vacuum is applied.

The abovementioned cooling of the treatment head 5 by means of air can be performed both during the actual emission of electrons and also during those periods of time in which no irradiation takes place.

All of the features disclosed in the application documents are claimed as essential to the invention in so far as they are novel individually or in combination with respect to the prior art.

The invention claimed is:

1. A method for sterilising containers, comprising the steps of moving a treatment head into an interior of a container to be sterilised and emitting radiation from the treatment head into the interior of the container at least intermittently over a predefined time period (dT), moving the container relative to the treatment head in a longitudinal direction (L) of the container at least intermittently at a relative movement speed (v) over the predefined time period (dT), varying the relative movement speed (v) of the treatment head in the interior of the container over the predefined time period (dT) and controlling movement of the treatment head as a function of an internal profile of the container, wherein movement of the treatment head is controlled by a control device on the basis of data stored in a memory device, which data are characteristic of cross-sections of the container in the longitudinal direction (L) of the container, and controlling the movement of the treatment head as a function of an angle at which the internal wall of the container extends relative to the longitudinal direction (L) of the container.

2. The method according to claim 1, comprising controlling movement of the treatment head as a function of a diameter D(L) of the container.

3. The method according to claim 1, comprising controlling movement of the treatment head on the basis of a programmed travel profile.

4. The method according to claim 1, comprising moving the container in its longitudinal direction (L).

5. The method according to claim 1, comprising determining a travel profile by guiding the treatment head into the interior of a container, moving the container relative to the treatment head in a longitudinal direction (L) of the container during the emission of the radiation, and recording data which are characteristic of radiation striking an internal wall of the container.

6. The method according to claim 5, comprising the step of applying a material which reacts to the radiation emitted by the treatment head and which allows conclusions to be drawn about an intensity of the radiation to an internal wall of the container.

7. The method according to claim 1, comprising the step of changing movement speed to adapt to different profiles of the container.

8. The method according to claim 1, wherein the treatment head comprises an electron emission source and an acceleration device, and including the step of accelerating the electrons towards an exit window.

9. The method according to claim 1, including the step of providing a shield in order to shield x-ray radiation.

10. The method according to claim 1, wherein container and the treatment head are arranged on the same transport device, and including the step of moving the container and the treatment head and are moved synchronously with one another.

11. The method according to claim 1, wherein the transport device comprises a transport carousel.

12. The method according to claim 1, wherein the treatment head comprises an exist window at its end side, and including the step of passing electrons through the exit window.

13. The method according to claim 12, wherein the exit window comprises a film having a thickness in a range from 7-13 μm.

14. The method according to claim 12, wherein the exit window comprises a titanium film.

15. The method according to claim 1, wherein a gaseous medium is used to cool an exit window of the treatment head.

16. The method according to claim 1, wherein movement of the container relative to the treatment head in a longitudinal direction (L) takes place within two (2) seconds.

17. The method according to claim 16, wherein movement of the container relative to the treatment head in a longitudinal direction (L) takes place within one (1) second.

18. The method according to claim 1, wherein the treatment time equals the treatment time during which the treatment head is located in the bottle.

19. The method according to claim 1, wherein the method total cycle time includes movement of the treatment head into the interior of the container, treatment time and movement of the treatment head out of the interior of the container.

20. The method according to claim 1, wherein the treatment head is moved into the interior of the container and movement stopped for a time period, and radiation is emitted both during movement of the treatment head and while the treatment head is stopped.

21. The method for determining a travel profile for a treatment head for the internal sterilisation of containers, comprising the steps of moving the treatment head into an interior of a container and directing radiation from the treatment head onto an internal wall of the container, moving the container relative to the treatment head in a longitudinal direction (L) of the container during the emission of the radiation, recording data which are characteristic of radiation striking an internal wall of the container, and controlling the movement of the treatment head as a function of an angle at which the internal wall of the container extends relative to the longitudinal direction (L) of the container.

22. The method according to claim 21, wherein movement of the container relative to the treatment head in a longitudinal direction (L) takes place within two (2) seconds.

23. The method according to claim 22, wherein movement of the container relative to the treatment head in a longitudinal direction (L) takes place within one (1) second.

24. The method according to claim 21, wherein the treatment time equals the treatment time during which the treatment head is located in the bottle.

25. The method according to claim 21, wherein the method total cycle time includes movement of the treatment head into the interior of the container, treatment time and movement of the treatment head out of the interior of the container.

26. The method according to claim 21, wherein the treatment head is moved into the interior of the container and movement stopped for a time period, and radiation is emitted both during movement of the treatment head and while the treatment head is stopped.

27. A method for sterilising containers, comprising the step of moving a treatment head into an interior of a container to be sterilised and emitting radiation from the treatment head into the interior of the container at least intermittently over a predefined time period (dT), moving the container relative to the treatment head in a longitudinal direction (L) of the container at least intermittently at a relative movement speed (v) over the predefined time period (dT), varying the relative movement speed (v) of the treatment head in the interior of the container over the predefined time period (dT) and controlling movement of the treatment head as a function of an internal profile of the container, wherein movement of the treatment head is controlled as a function of a diameter D(L) of the container.

28. The method according to claim 27, wherein movement of the container relative to the treatment head in a longitudinal direction (L) takes place within two (2) seconds.

29. The method according to claim 28, wherein movement of the container relative to the treatment head in a longitudinal direction (L) takes place within one (1) second.

30. The method according to claim 27, wherein the treatment time equals the treatment time during which the treatment head is located in the bottle.

31. The method according to claim 27, wherein the method total cycle time includes movement of the treatment head into the interior of the container, treatment time and movement of the treatment head out of the interior of the container.

32. The method according to claim 27, wherein the treatment head is moved into the interior of the container and movement stopped for a time period, and radiation is emitted both during movement of the treatment head and while the treatment head is stopped.

* * * * *

UNITED STATES PATENT AND TRADEMARK OFFICE
CERTIFICATE OF CORRECTION

PATENT NO.        : 8,821,788 B2                                            Page 1 of 1
APPLICATION NO.   : 12/546133
DATED             : September 2, 2014
INVENTOR(S)       : Krueger et al.

It is certified that error appears in the above-identified patent and that said Letters Patent is hereby corrected as shown below:

In the Claims,

Claim 10, Col. 11, line 2, "treatment head and are moved synchronously" should be --treatment head synchronously--.

Signed and Sealed this
Fourteenth Day of April, 2015

Michelle K. Lee
*Director of the United States Patent and Trademark Office*